United States Patent [19]

Kobayashi

[11] Patent Number: 4,781,453
[45] Date of Patent: Nov. 1, 1988

[54] OPHTHALMIC EXAMINATION APPARATUS

[75] Inventor: Koji Kobayashi, Hino, Japan
[73] Assignee: Kowa Company Ltd., Aichi, Japan
[21] Appl. No.: 49,719
[22] Filed: May 12, 1987
[30] Foreign Application Priority Data
 May 12, 1986 [JP] Japan .................. 61-106688
[51] Int. Cl.⁴ .............................. A61B 3/10
[52] U.S. Cl. .................... 351/205; 351/206; 351/221
[58] Field of Search ............... 351/205, 206, 211, 221

[56] References Cited
U.S. PATENT DOCUMENTS
 4,541,697  5/1983  Remisan ..................... 351/205 X Primary Examiner—Rodney B. Bovernick
Attorney, Agent, or Firm—Bruce L. Adams; Van C. Wilks

[57] ABSTRACT

An ophthalmic examination apparatus directs a laser beam from a laser light source onto the fundus of an eye to scan the fundus two-dimensionally, picks up the light reflected back from the eye fundus and by means of a photoelectric transducer subjects the light to photoelectric conversion to obtain information about the eye fundus. A laser light source is provided that generates laser beams of a plurality of wavelengths, a first acousto-optical device selects one wavelength from among the plurality of laser beam wavelengths, a first optical deflector is used to scan a laser beam in one direction at a predetermined frequency, and a second optical deflector is used for scanning the laser beam in a direction at right-angles to the above direction at a frequency that is lower than the above frequency. The first optical deflector is constructed as the second acousto-optical device which is driven at an ultrasonic frequency, and by changing the range of variability of the ultrasonic frequency of the second acousto-optical device in accordance with the laser beam wavelength selected by the first acousto-optical device, the angle of deflection of the first optical deflector becomes the same irrespective of the wavelength of the laser beam.

5 Claims, 2 Drawing Sheets

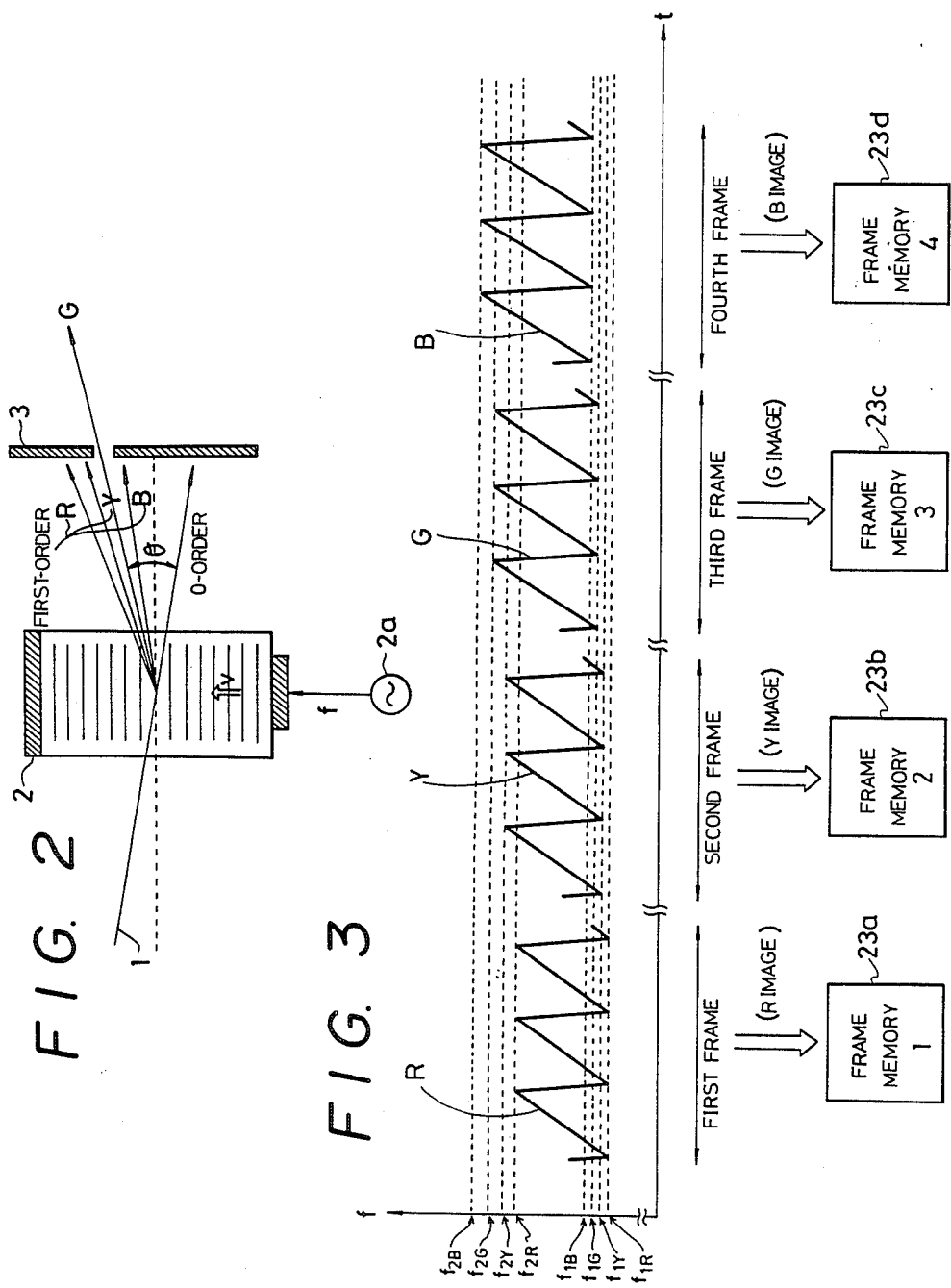

OPHTHALMIC EXAMINATION APPARATUS

BACKGROUND OF THE INVENTION

1. Field of the Invention

This invention relates to an ophthalmic examination apparatus, and more particularly to an electronic type ophthalmic examination apparatus which uses a laser beam for two-dimensional scanning of the eye fundus, collects the light reflected back from the eye fundus and subjects the light to photoelectric conversion to obtain information about the eye fundus.

2. Description of the Prior Art

Conventionally, in order to examine the eye fundus there are in wide use the method whereby the physician examines the patient's eye directly by means of an opthalmoscope, and the method whereby a special fundus camera is used to take photographs of the eye fundus. Also, with the advance in recent years of electronic technology, use is also being made of optoelectronic transducers such as imaging tubes and the like in place of the photographic film of the conventional fundus camera, eye fundus information is read out directly in the form of electric signals which are processed and stored in a memory or displayed on a monitor television or the like.

Of these conventional electronic examination apparatuses, one that employs laser scanning and which has developed by the Retina Foundation of the U.S. (see Applied Optics, vol. 19 (1980) page 2991) has attracted attention for the many features it possesses. Specifically, by replacing the light source conventionally used in the flying spot scanning type video image input system by a laser beam for eye fundus applications, restricting the incident light beam to a small zone in the center of the pupil and receiving, photoelectrically converting and amplifying the light reflected by the eye fundus from a larger area around the periphery of the pupil, it becomes possible to display on a monitor television a real-time video image of the eye fundus with a low brightness and a high S/N ratio. In addition, it becomes possible to decrease greatly the amount of fluorescent agent that is administered when fluorescent image photography of the eye fundus is to be performed. Also, by modulating the scanning laser beam it becomes possible to examine retina function in the course of observing the eye fundus image, and by utilizing the advantages of the laser beam's depth of focus, the elimination of corneal reflection due to polarization and the monochromatic nature of the light, it becomes possible to provide an excellent diagnostic apparatus.

The drawback with this type of apparatus is that the system for controlling the laser beam deflection is difficult. In the reference material cited in the above, two mechanical laser beam deflection systems are employed which are operated at scanning frequencies of 7.8 kHz for the horizontal scanning and 60 Hz for the vertical scanning. But, in order to obtain high-definition video images it is necessary to use higher laser beam scanning frequencies. In the case of laser beam deflection corresponding to standard NTSC raster scanning, the horizontal scanning frequency is 15.75 KHz, which is basically impossible to realize with a mechanical type of optical deflector from the standpoint of service life and durability.

The practical application was then tried of an idea that was announced which involved the use for the horizontal deflector of a non-mechanical acousto-optical device having no moving parts. If, however, the apparatus is to be used to obtain color information, because the acousto-optical device utilizes diffraction, the angle of deflection inherently differs in accordance with the color, and compensating for this requires an extremely complex optical system. In addition, each such type of optical system is effective only with respect to a set laser beam wavelength. Thus, as the eye fundus is comprised of a plurality of layers each of which has reflection characteristics that differ from those of the other layers with respect to a set wavelength, in order to accurately diagnose morbid portions it is necessary to observe the eye fundus with light of each of the necessary wavelengths. However, in the case where an acousto-optical device was employed for the laser beam deflection, it was impossible to change to a laser beam having any desired wavelength among an arbitrary plurality of wavelengths.

It is therefore an object of this invention to solve the aforementioned problems by providing an ophthalmic examination apparatus that enables the realization of a laser beam scanning system that makes it possible to realize high-frequency laser beam scanning, can be freely adapted to any arbitrary wavelength, allows color information to be obtained and has outstanding reliability and operability.

SUMMARY OF THE INVENTION

In order to solve the aforementioned problems, the present invention comprises an ophthalmic examination apparatus which directs a laser beam, generated by a laser light source, at a subject eye fundus to scan the fundus two-dimensionally, picks up the light reflected back from the eye fundus and by means of a photoelectric transducer subjects the light to photoelectric conversion to obtain information about the eye fundus. The apparatus comprises a laser light source that generates laser beams of a plurality of wavelengths;
- a first acousto-optical device which selects one wavelength from among the plurality of laser beam wavelengths;
- a first optical deflector for scanning a laser beam in one direction at a predetermined frequency; and
- a second optical deflector for scanning the laser beam in a direction that is at right-angles to the above said direction at a frequency that is lower than the above said frequency. The first optical deflector is constructed as the second acousto-optical device driven at an ultrasonic frequency, and by changing the range of variability of the ultrasonic frequency of the second acousto-optical device in accordance with the laser beam wavelength selected by the first acousto-optical device, the angle of deflection of the first optical deflector becomes the same irrespective of the wavelength of the laser beam. In the present invention for each image frame as determined by the scanning frequency of the second optical deflector the laser beam wavelength selected by the first acousto-optical device is also changed to obtain color information.

With the aforementioned construction, first, one out of a plurality of laser beam wavelengths is selected by means of an acousto-optical device and the range of variability of the ultrasonic driving frequency of another acousto-optical device is changed in accordance with the selected laser beam wavelength, so that the angle of deflection of the first optical deflector scanning the laser beam in one direction at a predetermined frequency can be made the same irrespective of the wavelength of the laser beam, thereby making high-speed laser beam scanning possible. In addition, the arrangement is such that the laser beam wavelength selected for each video image frame as determined by the scanning frequency of the second optical deflector which scans in a direction that is at right-angles to the scanning direction of the first deflector can be changed, so that by obtaining color information for each frame, such as for example red, yellow, green and blue color image information and storing this information in a memory or the like and synthesizing it afterward, it becomes possible to obtain color video images.

Thus, in accordance with the present invention, highly reliable control of the laser beam deflection at a high scanning frequency that corresponds to the raster scan of an ordinary television becomes possible, and with the scanning range it is possible to make the deflection constant regardless of the laser beam wavelength. As it is possible to freely select a laser beam of any desired wavelength from the laser light source, it also is possible to display images of a different layer of the eye fundus in a desired hue. Furthermore, when color images are to be obtained, unlike in the case of a system where laser beams of a plurality of wavelengths are beamed simultaneously, with the present invention, for each frame monochrome images at the selected single wavelength is obtained, and by afterward sythesizing these color images can be obtained. Thus, an excellent ophthalmic examination apparatus can be obtained that reduces the burden on the patients eye and decreases the cost because a single photosensor suffices.

BRIEF DESCRIPTION OF THE DRAWINGS

The objects and features of the present invention will become more apparent from the following detailed description taken in conjunction with the accompanying drawings in which:

FIG. 2 is an explanatory diagram showing the operating principle of wavelength selection by means of color dispersion produced by the acousto-optical deflector; and FIG. 3 is a diagram of a signal waveform to explain the operation of the apparatus according to the present invention.

DETAILED DESCRIPTION OF THE PREFERRED EMBODIMENTS

Figure 1:
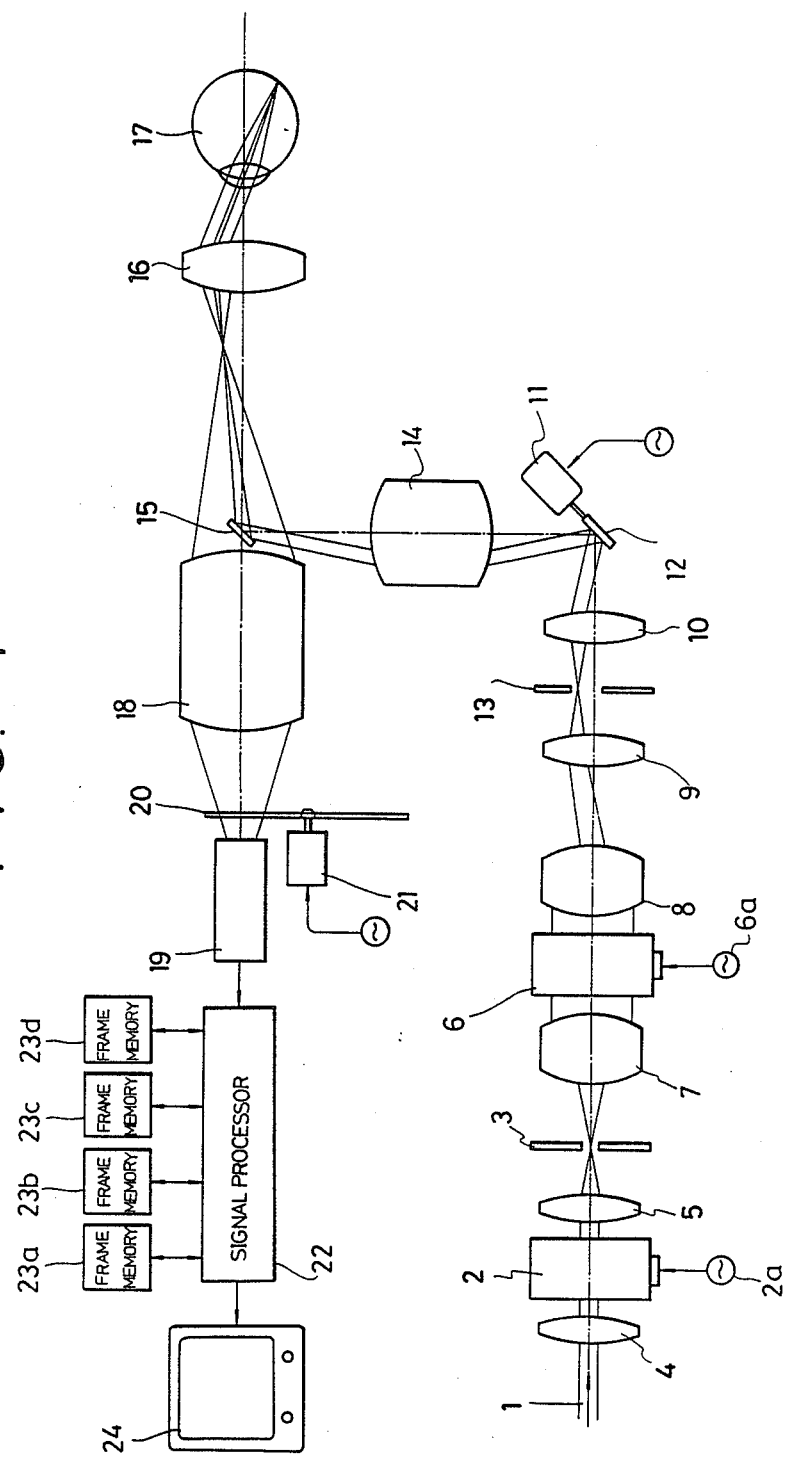
FIG. 1 is a schematic diagram showing the overall structure of an ophthalmic examination apparatus according to the present invention.

With reference to the schematic diagram of FIG. 1 showing the general construction of an ophthalmic examination apparatus according to the present invention, the numeral 1 denotes a laser beam which includes a plurality of wavelengths such as, for example, that of red, yellow, green and blue light synthesized from a laser light source (not shown) such as helium-neon (He-Ne), argon (Ar+), krypton (Kr+) or the like. The laser beams 1 impinge via a lens 4 on a wavelengthselection first acousto-optical device 2. As shown in FIG. 2, when the first acousto-optical device 2 is driven at an ultrasonic frequency f by means of a signal source 2a, when the laser beam 1 having a plurality of wavelengths impinges on the first acousto-optical device 2 and wavelength selection is performed through the color dispersion, if the laser beam wavelength is $\lambda$, the ultrasonic frequency f and the ultrasonic velocity is v, then the angle of deflection $\theta$ of the laser beam can be expressed as $\theta = \lambda f / v$, so that by varying f it is possible to select only light which is of a predetermined wavelength. In order to effectively select this specific wavelength, the laser beam is deflected by the first acousto-optical device 2 onto a slit 3 via a lens 5, cutting off light of other wavelengths. Also, by varying the electrical power of the signal source 2a, the first acousto-optical device 2 can be used to intensity-modulate the laser beam to project a fixation target or desired index for examination of retinal functions onto the eye fundus.

What has become a single-wavelength laser beam by passage through the slit 3 impinges on a second acousto-optical device 6 of the same construction as the first acousto-optical device 2 and which is driven by a signal source 6a. Here, the frequency which changes the ultrasonic frequency f is selected as, for example, the 15.75 kHz of the ordinary television horizontal scan, so that the laser beam is thus deflected at this frequency and (horizontally) scans the eye fundus at this frequency.

Lenses 7 and 8 are disposed one at each end of the second acousto-optical device 6 and the laser beam is thereby shaped for impingement on the rectangular opening of the second acousto-optical device 6, to obtain a shaped laser beam exiting therefrom. The laser beam deflected for horizontal scanning by means of the second acousto-optical device 6 is guided via relay lenses 9 and 10 to a mirror 12 (a galvanomirror) mounted on a galvanometer 11. Provided between the lenses 9 and 10 is a slit 13 which cuts off zero-order light coming from the second acousto-optical device 6 and allows only first-order diffraction light to pass. The galvanomirror is driven at, for example, 60 Hz in synchronization with the vertical scan rate of an ordinary television, to deflect the laser beam vertically for scanning.

After the laser beam that thus scans in the two dimensions, horizontally and vertically, has passed through a lens 14 it is reflected by a mirror 15 and directed at an object lens 16 by means of which it is directed through the center portion of the pupil of the eye 17 being examined and impinges on the eye fundus. The light reflected from the eye fundus passes back though the object lens 16, and by means of a condenser lens 18 is condensed onto the photosensitive surface of a photosensor 19. Disposed at the front face of the photosensor 19 is a filter 20 corresponding to the wavelength of the laser beam selected by means of the first acousto-optical device 2. The filter 20 is arranged so that it can be selectively interposed by the rotation of a motor 21. The first acousto-optical device 2 can for example change laser beam wavelengths for each frame, and the filter is selected to allow passage of the selected light by the synchronized rotation of the motor 21.

The electrical signals which have been produced by the photoelectrical conversion by the photosensor 19 carry eye fundus information which is stored in a frame memory 23 by means of a signal processing circuit 22. This frame memory is comprised of, for example, frame memories 23a to 23d for storing red, yellow, green and blue image information. The images processed by the signal processing circuit 22 can be displayed on a monitor television 24.

The operation of the apparatus according to the present invention constructed as described in the foregoing will now be explained.

First, the laser light source is activated to generate the laser beam 1 possessing a number of wavelengths. The laser beam 1 is made to impinge on the first acousto-optical device 2 via the lens 4. At this point, by activating the signal source 2a, as shown in FIG. 2, only the light of the prescribed wavelength as selected by the slit 3 is allowed to pass. The laser beam passing through the slit 3 is deflected by the second acousto-optical device 6 for horizontal scanning. The scanning frequency is related to changes in the ultrasonic frequency of the signal source 6a, but because in this case the angle of deflection $\theta$ depends on the wavelength of the laser beam ($\theta = 80 \, f/v$), each time the laser beam wavelength selected by the first acousto-optical device 2 changes, the scanning range is changed.

Therefore, with this invention, in order to compensate for this the range of variation of the ultrasonic frequency that drives the second acousto-optical device 6 is changed to $f_{1R} - f_{2R}$ in the case of a red laser beam wavelength, $f_{1Y} - f_{2Y}$ in the case of yellow, $f_{1G} - f_{2G}$ in the case green and $f_{1B} - f_{2B}$ in the case of blue. As a result, when the eye fundus of an eye 17 that is being examined is scanned via the lenses 8 and 9, slit 13, lens 10, mirror 12, lens 14, mirror 15 and object lens 16, it becomes possible to control the range of the horizontal scanning so that it becomes the same.

In cases where color images are to be obtained, as the laser light source, when using for example the four colors, red, yellow, green and blue, as shown by FIG. 3, the first acousto-optical device 2 is used for the sequential selection of a different laser beam wavelength every other frame. When the selected laser beam is projected onto the fundus of the eye 17 and information therefrom is extracted, the signals coming from the photosensor 19 are processed by the signal processing circuit 22 and, assuming for example that it is the red light laser beam that has been selected, the red image information will be stored in the frame memory 23a. Likewise, if yellow has been selected it will be stored in the frame memory 23b; if green, in the frame memory 23c; and if blue, in the frame memory 23d. At this time, the filter 20 interposed in correspondence to the selected laser beam wavelength by the synchronized rotation of the motor 21. Finally, a four-frame time period is applied and four frames of monochromatic eye fundus images are obtained, and by selecting the desired images from among them and displaying said images on the monitor 24, it becomes possible to display images of different layers of the eye fundus in a desired hue.

In addition, because in the present invention control for selection of the laser beam wavelength is entirely electronic, even if the laser beams of a wavelength not used previously appear and is to be used in the near future, there is no need to make any special changes to the optical system other than the filters with the result that adaption thereto is extremely simple.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmic examination apparatus which directs a laser beam from a laser light source at a subject eye fundus to scan the fundus two-dimensionally, picks up the light reflected back from the eye fundus and by means of a photoelectric transducer subjects the light to photoelectric conversion to obtain information about the eye fundus, said apparatus comprising:
   a laser light source that generates laser beams of a plurality of wavelengths;
   a first acousto-optical device which selects one wavelength from among the plurality of laser beam wavelengths;
   a first optical deflector for scanning a laser beam in one direction at a predetermined frequency; and
   a second optical deflector for scanning the laser beam in a direction that is at right-angles to the above said direction at a frequency that is lower than the above said frequency;
   wherein said first optical deflector is the second acousto-optical device driven at an ultrasonic frequency, and by changing the range of variability of the ultrasonic frequency of the second acousto-optical device in accordance with the laser beam wavelength selected by the first acousto-optical device, the angle of deflection of the first optical deflector becomes the same irrespective of the wavelength of the laser beam.

2. The ophthalmic examination apparatus according to claim 1, wherein the first acousto-optical device is also provided with the function of intensity-modulation of the laser beam and projection of an index onto the eye fundus.

3. An ophthalmic examination apparatus which directs a laser beam from a laser light source at a subject eye fundus to scan the fundus two-dimensionally, picks up the light reflected back from the eye fundus and by means of a photoelectric transducer subjects the light to photoelectric conversion to obtain information about the eye fundus, said apparatus comprising:
   a laser light source that generates laser beams of a plurality of wavelengths;
   an acousto-optical device which selects one wavelength from among the plurality of laser beam wavelengths;
   a first optical deflector for scanning a laser beam in one direction at a predetermined frequency; and
   a second optical deflector for scanning the laser beam in a direction that is at right-angles to the above said direction at a frequency that is lower than the above said frequency;
   wherein for each image frame as set by the predetermined scanning frequency of the second optical deflector the laser beam wavelength selected by the first acousto-optical device is changed to obtain color information.

4. The ophthalmic examination apparatus according to claim 3, wherein for each frame different eye-fundus color information is obtained, stored in a memory and then synthesized to obtain color images.

5. The ophthalmic examination apparatus according to claim 3, wherein a filter which transmits the selected laser light is provided sequentially in front of the photoelectric transducer in synchronization with the laser light wavelength selection.

* * * * *